(12) United States Patent
Sauer et al.

(10) Patent No.: US 7,311,715 B2
(45) Date of Patent: Dec. 25, 2007

(54) SUTURING SET FOR MEDICAL USE

(75) Inventors: Michael Sauer, Tuttlingen (DE); Martin Oberlaender, Tuttingen (DE)

(73) Assignee: Karl Storz GmbH & Co. KG (DE)

(*) Notice: Subject to any disclaimer, the term of this patent is extended or adjusted under 35 U.S.C. 154(b) by 722 days.

(21) Appl. No.: 10/854,827

(22) Filed: May 27, 2004

(65) Prior Publication Data
US 2005/0165417 A1 Jul. 28, 2005

Related U.S. Application Data

(63) Continuation of application No. PCT/EP02/12236, filed on Nov. 2, 2002.

(30) Foreign Application Priority Data
Nov. 27, 2001 (DE) .............................. 101 58 142

(51) Int. Cl.
*A61B 17/04* (2006.01)
(52) U.S. Cl. .................................................. 606/148
(58) Field of Classification Search ................ 606/139, 606/148, 144, 147, 222, 224, 228, 232
See application file for complete search history.

(56) References Cited
U.S. PATENT DOCUMENTS

| | | |
|---|---|---|
| 919,138 A | 4/1909 | Drake et al. |
| 962,218 A | 6/1910 | Heitz-Boyer |
| 2,808,055 A | 10/1957 | Thayer .................... 128/340 |
| 3,013,559 A | 12/1961 | Thomas ................... 128/340 |
| 3,361,382 A | 1/1968 | Converse ................ 242/137.1 |
| 4,012,010 A | 3/1977 | Friedman ................ 242/129.8 |
| 5,928,252 A | 7/1999 | Steadman et al. .......... 606/148 |

FOREIGN PATENT DOCUMENTS

| | | |
|---|---|---|
| FR | 952.119 | 11/1949 |
| FR | 1.069.680 | 7/1954 |
| JP | 11-334 | 1/1999 |
| WO | WO 00/67643 | 11/2000 |

*Primary Examiner*—Michael J. Hayes
*Assistant Examiner*—Victor Nguyen
(74) *Attorney, Agent, or Firm*—St. Onge Steward Johnston & Reens LLC

(57) ABSTRACT

The invention relates to a suturing set for medical use, comprising a handle piece, a needle, at least partly embodied as a hollow needle and which may be fixed to the handle and a transport device, arranged within the handle, which may be displaced between two end positions for the supply of suturing material to the needle, whereby the transport device comprises a gripping device, by means of which the supplied suturing material may be grasped in one end position of the transport device and then released in the other end position of the transport device. According to the invention, the transport of the suturing material to the needle may be achieved in a simple, secure and material-protective manner, whereby the introduced suturing material, on reaching an end position of the transport device, is gripped in a clamping manner by means of displacing the transport device and is only released again on reaching the other end position of the transport device.

11 Claims, 3 Drawing Sheets

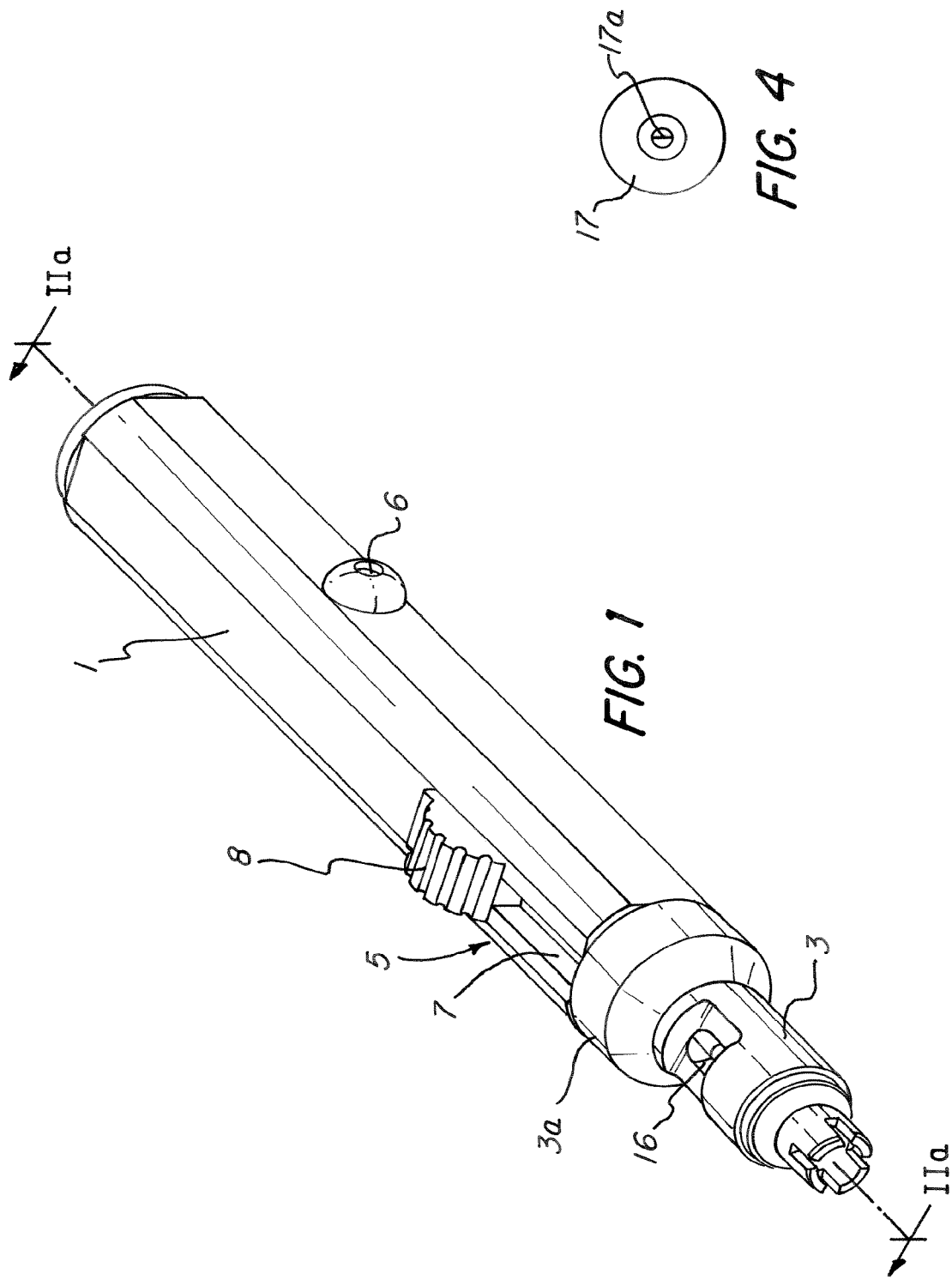

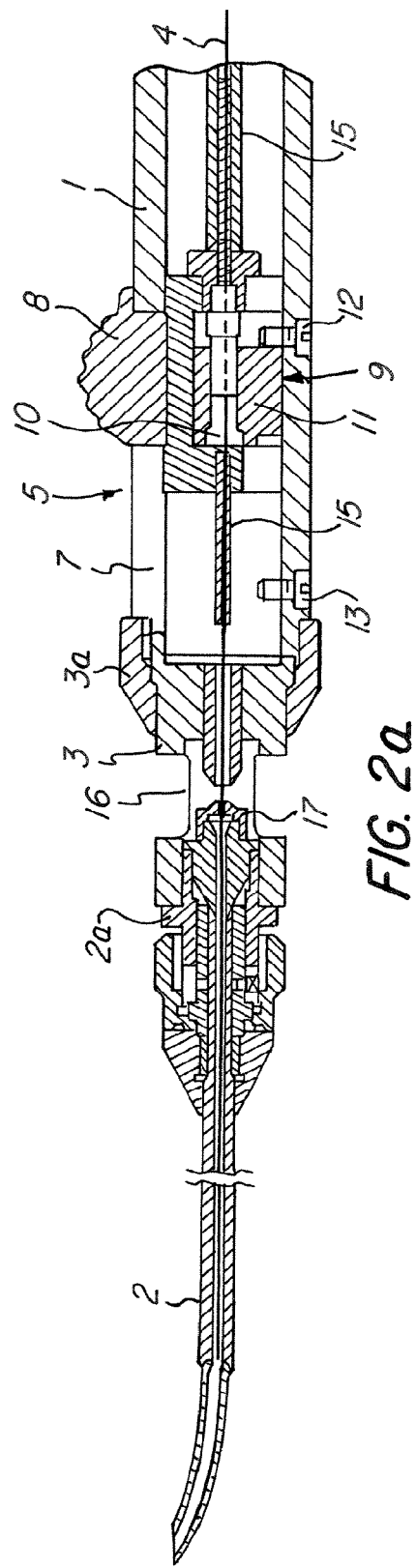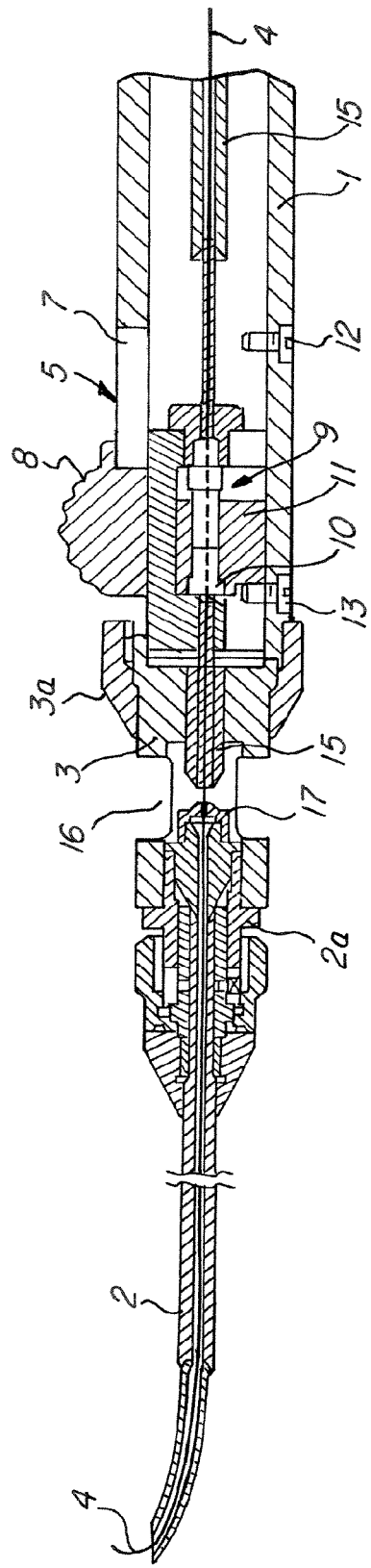

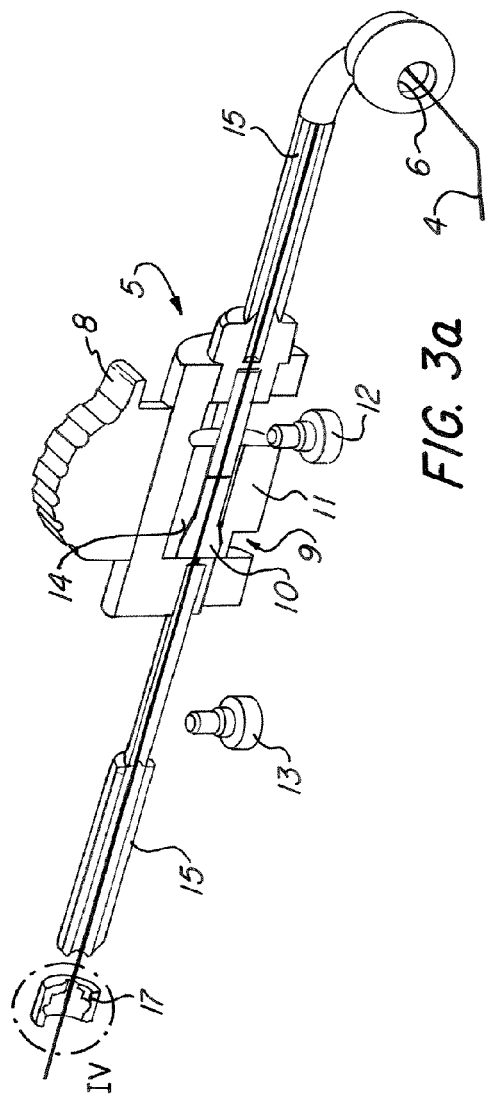
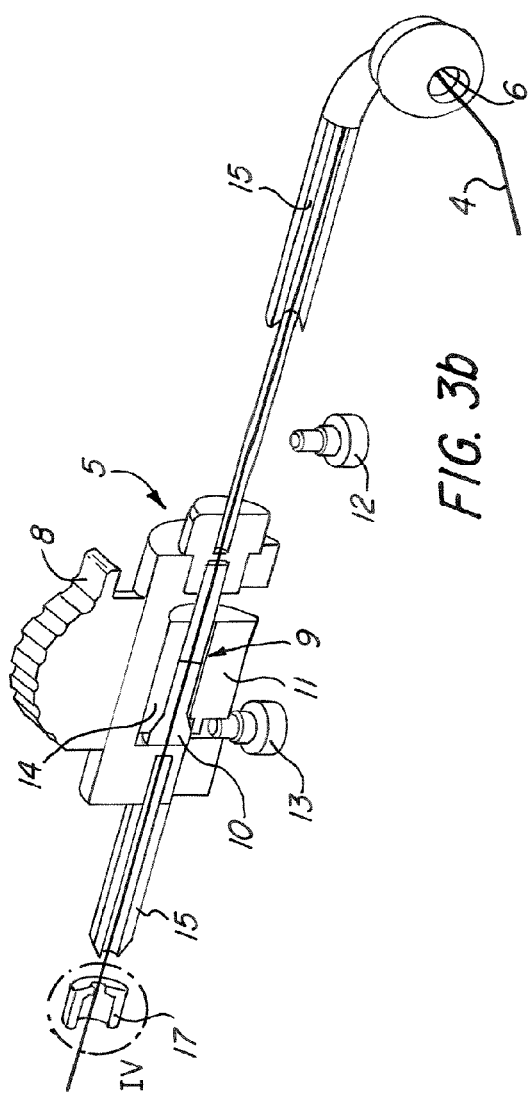

SUTURING SET FOR MEDICAL USE

This application is a continuation of pending International Patent Application No. PCT/EP02/12236 filed Nov. 2, 2002 which designates the United States and claims priority of pending German Application No. 101 58 142.4 filed Nov. 27, 2001.

FIELD OF THE INVENTION

The invention relates to a suturing set for medical purposes, having a handle, a needle that can be secured to the handle and is configured, at least partly, as a hollow needle, as well as a conveyor member that is mounted on the handle and can slide between two end positions to conduct suturing material to the needle. The conveyor member has a clamping device by means of which the inserted suturing material can be gripped in an end position of the conveyor member by clamping and can be released again in the other end position of the conveyor member.

A conventional suturing set is described, for instance, in FR 1069680A. In the surgical suturing set described in said publication, the conveyor member consists of a slide device, positioned so that it can slide in a groove, and consists of two plates which are distanced from one another by springs. Between the two plates of the slide device a tube is installed for conducting the suturing material. To move the slide device and to clamp the suturing material inside the tube, the upper plate has a push button, by means of which this plate can be positioned against the force of the spring in the direction of the lower plate. When the push button is activated, the tapering pointed conical end of the push button enters into the tube through an aperture and secures the suturing material that is contained in the tube. Now, when the push button is pushed, the slide device can be moved together with the tube gripped by the conical continuation of the push button and with the suturing material.

This conventional device allows material to be protected during conveyance for the most part, but has the disadvantages, first, that the push button must be held pressed down for the entire time during which the button is advanced, in order to move the suturing material with it, and, second, there is the risk that the push button is pushed down when the slide device is pushed back, and thus the suturing material is gripped again and pulled out of the needle.

An additional suturing set is described in U.S. Pat. No. 2,808,055. In this suturing set, the conveyor member consists of a guide shoe that can be slid in a groove of the handle, with a tubular extension. The guide shoe and the extension have a continuous aperture to receive the suturing material. When the guide shoe is slid, the extension of the guide shoe is pushed into the hollow needle or is withdrawn from it again.

The suturing material is conveyed to the needle, in this known arrangement, as follows: the suturing material, starting from a yarn bobbin positioned in the handle, is first pulled out of the handle, so that it can then be inserted through a thread aperture into the continuous aperture of the guide shoe of the transport device. When the guide shoe is slid all the way to the needle, the operator of the suturing set must firmly grip the suturing material with one finger bent on the thread aperture, to ensure that the suturing material is also carried along when the guide shoe is slid forward. The suturing material fed in this way into the hollow needle by means of the guide shoe and the tube-shaped extension is then jammed by friction in the distal narrow part of the hollow needle in such a way that the guide shoe can be pushed back again without pulling the suturing material out of the hollow needle again.

One disadvantage of this known suturing set is that the conveyance of the suturing material all the way to the needle is possible only if the operator of the set holds the suturing material clamped to the thread aperture. As a result, first, the operator of the set is restricted in the handling of the suturing set, and, second, there is the risk that the suturing material can be damaged in the snapping and clamping. In addition, replacing the suturing material, in this arrangement, requires considerable time and installation effort, since the handle must be taken apart to replace the yarn bobbin.

As a result, it is the object of this invention to perfect a suturing set of the aforementioned type in such a way that the suturing material is conveyed to the needle in a manner that is simple, safe, and economical in terms of material. In order to achieve this object, the present invention is characterized by the fact that, on reaching an end position of the conveyor member by sliding the conveyor member, the inserted suturing material is held by gripping and is not released again until it reaches the other end position of the conveyor member.

As a result of the inventive arrangement of the conveyor member with a clamping device for the suturing material, it is possible for the first time, after an initial manual insertion of the suturing material, to finish conveying the suturing material all the way to the needle without further manual handling of the suturing material. Here, the clamping device advantageously consists of at least one forceps part that can be re-shaped elastically in a radial direction, surrounding the suturing material, and at least one clamping element that can be pushed upward relative to the forceps part and onto the forceps part. As soon as the at least one clamping element is slid onto the at least one forceps part, the forceps part is radially re-shaped in such a way that the suturing material inserted in the forceps part is secured by clamping by the forceps part.

The least one clamping element is slid relative to the at least one forceps part, in a preferred embodiment of the invention, in such a way that when the conveyor member reaches the one end position, the clamping element is pushed up onto the forceps part and when the conveyor member reaches the other end position, the clamping element is pushed downward again by the forceps part.

In a practical embodiment of the invention, it is proposed that the clamping device is positioned inside a slide device that can be displaced manually between the two end positions of the conveyor member.

According to a practical embodiment of the invention, stops, which are positioned in the handle and in contact with the slidable clamping element, define the end positions of the conveyor member.

Pushing up the at least one clamping element onto the at least one forceps part can be facilitated if run-up slopes are configured on the forceps part and/or on the clamping element.

According to a preferred embodiment of the invention, the needle can be secured to the handle by an adapter piece. To be able to observe whether the conveyor member has correctly drawn up the suturing material and conveyed it, free of snapping, to the needle, at least one aperture is configured in the adapter piece to allow a view of the suturing material.

In addition, it is proposed with the invention that in the transition area from the adapter piece to the needle, an insulating cap should be installed, equipped with a slit for passage of the suturing material. This insulating cap, which, at least in the vicinity of the slit, should consist of an elastic material, especially a rubber or plastic, serves, first, to seal the proximal end of the needle and, second, with the passage slit for the suturing material serves as clamping and holder for the inserted suturing material, because the clamping in the slit prevents the suturing material from being pulled out of the needle again when the conveyor member is withdrawn, despite the open forceps parts, because of friction in the tube system of the conveyor member.

To conduct and stabilize the suturing material inside the suturing set, hollow tubes, or at least sections of tube, are situated in the handle and in the adapter piece to receive the suturing material. These hollow tubes prevent snapping and damaging of the suturing material.

It is finally proposed, with the invention, that to insert the suturing material into the handle and the conveyor member, a thread aperture consisting of a radial borehole is made in the handle. Any type of suturing material can be inserted into the conveyor member from outside by means of this thread aperture.

Additional objects and advantages of invention may be realized by means of the following description of the attached drawings, in which an embodiment of an inventive suturing set is presented in summary fashion.

BRIEF DESCRIPTION OF THE DRAWINGS

FIG. 1 is a perspective view of a handle of a suturing set according to the invention.

FIG. 2a is a cutaway longitudinal section along the cutting line IIa-IIa, according to FIG. 1 through the handle with needle inserted, showing the conveyor member in the farther end position.

FIG. 2b is a cutaway view as in FIG. 2b but showing the conveyor member in the closer end position.

FIG. 3a is a cutaway perspective detail view of the feeding of the suturing material, showing the conveyor member in the farther end position.

FIG. 3b is a perspective detail view according to FIG. 3a, but showing the conveyor member in the closer end position.

FIG. 4 is an enlarged and completed front view of the detail IV according to FIGS. 3a and 3b.

DETAILED DESCRIPTION OF EMBODIMENTS

FIG. 1 shows a perspective view of a handle 1 of a suturing set for medical purposes. To complete the suturing set, a needle 2 can be secured to the handle 1; this needle 2, in the embodiment illustrated in FIGS. 2a and 2b, is configured as a hollow needle equipped with a continuous aperture. As can also be seen from FIG. 1 as well as FIGS. 2a and 2b, in this illustrated embodiment the handle 1 and the needle 2 are connected to one another by means of an inserted adapter piece 3, and the adapter piece 3 is connected with the handle 1 by means of a screw cap 3a, and the needle 2 can be secured on the adapter piece 3 by means of an aperture 2a.

In order to thread suturing material 4 into the needle 2, a conveyor member 5 is positioned in the handle, and by means of this device, starting from a thread aperture 6 in the handle 1, the suturing material 4 can be conveyed to the needle 2. The structure of the conveyor member can be seen in detail in the illustrations of FIG. 2a to FIG. 3b.

The conveyor member 5 that can be slid between two end positions consists essentially of a slide device 8 positioned in an elongated hole 7 of the handle 1 and a clamping device 9, which in turn consists of at least one forceps part 10 and at least one clamping element 11. For gripping the suturing material 4, the forceps part 10 enclosing the suturing material 4 consists of a radially elastically malleable material, such as for instance a plastic material. The forceps part 10 is radially re-shaped by means of the clamping element 11, which is positioned in the slide device 8 of the conveyor member 5 so that it can be pushed relative to the forceps part 10, in such a way that the clamping element 11 can be pushed onto the forceps part 10 and can be pushed down again by it.

The end positions, between which the conveyor member 5 for moving the suturing material 4 to the needle 2 can travel inside the handle 1, are defined by stops 12 and 13, which, as can be seen from FIGS. 2a and 2b, are positioned in the handle 1. As can be seen from FIGS. 2a to 3b, when the conveyor member 5 comes in contact with the stops 12 and 13, it pushes the clamping element 11 relative to the forceps part 10 in such a way that when the clamping element 11 comes in contact with the farther stop 12, the element is pushed onto the forceps part 10, and on coming in contact with the closer stop 13, the clamping element is pushed back down again by the forceps part 10.

As a result of the radial shapability of the forceps part 10, the pushing of the clamping element 11 causes the suturing material, conducted in the forceps part 10, to be grasped by clamping by forceps part 10 until this clamping effect is released again on the other end position of the conveyor member 5, if the stop 13 pushes the clamping element 11 down from the forceps part 10 again.

To facilitate the pushing of the clamping part 11 onto the forceps part 10, in the illustrated embodiment run-up slopes 14 are configured on the forceps 10. It is also possible, of course, to configure run-up slopes 14 only on the clamping element or both on the forceps part 10 and on the clamping element.

The suturing material 4 is threaded into the needle 2 in the illustrated suturing set as follows:

The respective suturing material 4 is fed into the handle 1 by means of the thread aperture configured as a radial borehole. To stabilize and guide the suturing material, inside the handle 1 and the adapter piece 3, hollow tubes 15, or at least hollow sections of tubing, are installed, which receive and guide the suturing material.

At the start of the threading, the slide device 8 and thus the conveyor member 5 must be in the farther end position illustrated in FIGS. 1, 2a, and 3a. The suturing material 4 is now inserted by hand, through thread aperture 6, into the handle 1 until resistance can be felt. Then the conveyor member 5 is pushed by the slide device 8 to the far end position on the stop 13. In this end position the forceps part 10 of the clamping device opens again, so that the suturing material 4 can be inserted again by hand into the handle 1.

The suturing material 4 that has been thus manually inserted into the handle 1 now reaches the adapter piece 3. As can be seen from FIG. 1 as well as FIGS. 2a and 2b, at least one aperture 16 is made in the adapter piece 3 to provide a free view of the introduced suturing material 4. As soon as the suturing material 4 can be recognized through the aperture 16, manual insertion of the suturing material 4 can stop. Additional conveyance of suturing material 4 is now provided entirely by the conveyor member 5. The conveyor member 5, with opened forceps part 10 of the clamping device 9, is moved from the front end position back to the farther end position, until the stop 12 pushes the clamping element 11 onto the forceps part 10 again and thus the suturing material 4 is secured in the clamping device 9.

Upon additional pushing of the conveyor member 5 to the closer end position, the suturing material 4 is secured by clamping and moved farther in the direction of the needle 2. On contacting the front stop 13, the clamping element 11 is again pushed downward by the forceps part 10, so that the conveyor member 5 can be pushed back into the farther end position, without withdrawing the suturing material 4 again. This transport process continues until the suturing material 4 emerges from the point of the needle 2.

Accidental pulling of the suturing material 4 out of the needle 2, in the illustrated embodiment of a suturing set, is further prevented because in the transition area between the adapter piece 3 and the needle 2, an insulating cap 17 is positioned. A slit 17a is made in this cap for passage of the suturing material 4. Especially in the area of the slit 17a, this insulating cap 17 consists of a rubber or plastic material. Because of friction between the suturing material 4 and the side walls of the slit 17a which are in contact with the suturing material 4, pulling the suturing material 4 out of the needle 2 upon withdrawing the conveyor member 5 is avoided.

A suturing set of this design is distinguished in that the threading of the suturing material 4 after the initially manual insertion is completely mechanical, without manual contact on the suturing material 4 and in addition without snapping the suturing material 4.

REFERENCE KEY 1 handle
2 needle
2a aperture
3 adapter piece
3a screw cap
4 suturing material
5 conveyor member
6 thread aperture
7 elongated hole
8 slide device.
9 clamping device
10 forceps part
11 clamping element
12 stop
13 stop
14 run-up slope
15 hollow tube
16 aperture
17 insulating cap
17a slit

What is claimed is:

1. A suturing set for medical purposes, having a handle, a needle that can be secured to the handle and is configured, at least partly, as a hollow needle, as well as a conveyor member that is mounted on the handle and can slide between two end positions to conduct slack, bendable suturing material to the needle, wherein the conveyor member has a clamping device by means of which the inserted suturing material can be gripped in an end position of the conveyor member by clamping and can be released again in the other end position of the conveyor member, and wherein the suturing set is distinguished in that, on reaching an end position of the conveyor member by sliding the conveyor member, the inserted suturing material is held by gripping and is not released again until it reaches the other end position of the conveyor member.

2. A suturing set as in claim 1, wherein the clamping device is positioned inside a slide device that can be displaced manually between the two end positions of the conveyor member.

3. A suturing set as claim 1, wherein stops positioned in the handle define the end positions of the conveyor member.

4. A suturing set as in claim 3, wherein the stops engage with the displaceable clamping element.

5. A suturing set as in claim 4, wherein run-up slopes are configured on the forceps part and/or on the clamping element.

6. A suturing set as in claim 5, wherein the needle can be secured to the handle by means of an adapter part.

7. A suturing set as in claim 6, wherein at least one aperture is configured in the adapter part allowing a free view of the suturing material.

8. A suturing set as in claim 7, wherein an insulating cap with a slit for passage of the suturing material is positioned in the transition area from the adapter part to the needle.

9. A suturing set as in claim 8, wherein the insulating cap, at least in the area of the slit, is made of an elastic material, in particular rubber or plastic.

10. A suturing set as in claim 6, wherein hollow tubes, at least in sections, are positioned in the handle and the adapter part to guide the suturing material.

11. A suturing set as in claim 10, wherein the suturing material can be inserted into the handle and the conveyor member by means of a thread aperture configured as a radial bore hole.

* * * * *